United States Patent [19]
O'Connor et al.

[11] Patent Number: 5,770,125
[45] Date of Patent: Jun. 23, 1998

[54] HAPTIC ATTACHMENT SYSTEM FOR INTRAOCULAR LENSES USING DIODE LASER

[75] Inventors: John J. O'Connor, Rowland Heights; Lawrence Y. Wissman, Anaheim Hills, both of Calif.

[73] Assignee: Mentor Corporation, Santa Barbara, Calif.

[21] Appl. No.: 562,658

[22] Filed: Nov. 27, 1995

[51] Int. Cl.$^6$ ............................................. B29D 11/00
[52] U.S. Cl. ............................ 264/1.37; 219/121.66; 219/121.78; 264/1.7; 264/482; 264/155
[58] Field of Search ............................ 264/1.37, 1.7, 264/482, 155; 219/121.61, 121.64, 121.66, 121.78; 425/174.4

[56] References Cited

U.S. PATENT DOCUMENTS

| | | | |
|---|---|---|---|
| 4,056,855 | 11/1977 | Kelman . | |
| 4,104,339 | 8/1978 | Fetz et al. . | |
| 4,118,808 | 10/1978 | Poler . | |
| 4,786,445 | 11/1988 | Portnoy et al. | 264/1.37 |
| 4,790,846 | 12/1988 | Christ et al. . | |
| 4,843,209 | 6/1989 | Milligan . | |
| 4,863,539 | 9/1989 | Lee et al. . | |
| 4,888,013 | 12/1989 | Ting et al. . | |
| 4,894,062 | 1/1990 | Knight et al. . | |
| 4,978,354 | 12/1990 | Van Gent . | |
| 5,075,195 | 12/1991 | Babler et al. | 264/482 |
| 5,118,452 | 6/1992 | Lindsey et al. . | |
| 5,185,107 | 2/1993 | Blake . | |
| 5,250,235 | 10/1993 | Cook et al. | 264/1.37 |
| 5,252,262 | 10/1993 | Patel | 264/1.37 |
| 5,523,029 | 6/1996 | Korgel et al. | 264/1.7 |

FOREIGN PATENT DOCUMENTS 63-206240  8/1988  Japan .

*Primary Examiner*—Mathieu D. Vargot
*Attorney, Agent, or Firm*—Christie, Parker & Hale, LLP

[57] ABSTRACT

A system for staking a haptic to an optic to form an intraocular lens using a laser beam operating near the infrared range with a coaxial aiming laser beam operating in the visible range. A portion of the haptic is inserted into the optic through a radial bore and is exposed through an axial bore spanning from the optic upper surface to the radial bore. The coaxial laser beams are collimated and then focused using a microscope objective through the axial bores, onto the exposed haptic. Aiming of the coaxial beams onto the optic and haptic is aided by the use of a magnifying CCD camera positioned with its optical axis at a 45° angle to the optic horizontal plane. The coaxial lasers, which are typically focused to a minor diameter which is greater than or equal to the inner diameter of the axial bore, make contact with the exposed haptic. Consequently, the haptic is melted and is then allowed to cool, coalescing into a bead staking the haptic to the optic.

10 Claims, 4 Drawing Sheets

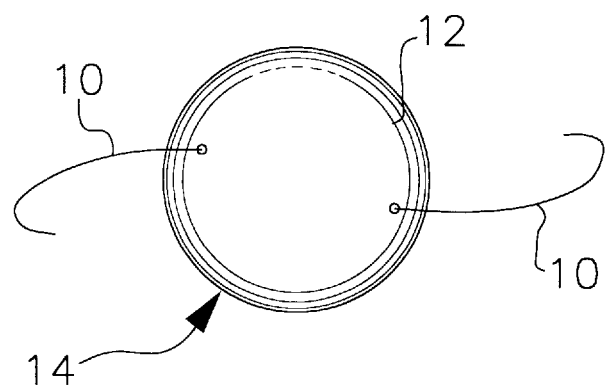
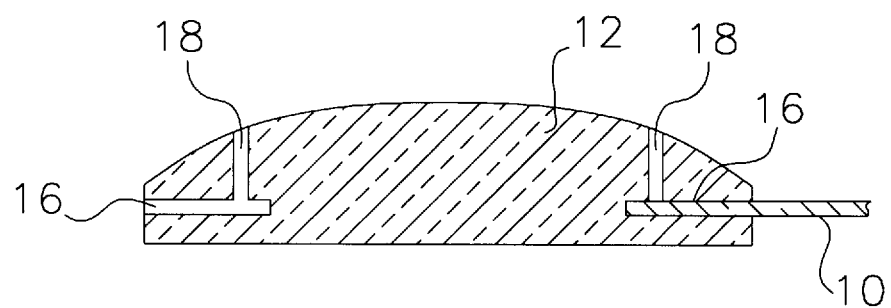

HAPTIC ATTACHMENT SYSTEM FOR INTRAOCULAR LENSES USING DIODE LASER

BACKGROUND OF THE INVENTION

The present invention relates to intraocular lenses and more specifically to a system for staking a haptic to an optic using a laser beam having a wavelength near the infrared region.

Various systems are currently being used for attaching haptics to optics to form intraocular lenses through staking. Some of these systems require that a radial bore be drilled into the optic, as well as, an axial bore from the optic upper surface intersecting the radial bore. An end portion of the haptic is then inserted into the optic through the radial bore until a portion of the inserted haptic is exposed through the axial bore. A heat source is then used to apply heat through the axial bore to melt the exposed haptic. After melting, the exposed haptic cools and coalesces into a bead, staking the haptic into the optic.

One current system for staking uses a Xenon photocoagulator as a heat source. The photocoagulator, which uses a Xenon arc lamp as a heat source, is an energy inefficient way of staking haptics to optics. When operating at peak output, the photocoagulator requires 5500 watts of power (220 VAC, 30 amps). Other systems use a Nd:YAG laser to transmit a laser beam through the axial bore to heat and melt the haptic. The Nd:YAG lasers, which operate in the infrared region at approximately a 1060 nm wavelength, are thermally efficient. However, when used for staking, their high thermal efficiency causes the haptic material to rapidly heat, resulting in nonuniform heating of the haptic. Nonuniform heating causes a weaker staking bond between the haptic and the optic. Furthermore, the Nd:YAG lasers are fairly expensive and require complex optics to deliver and focus the laser beam from the laser source onto the haptic. Due to the specialized optics, the operation of an Nd:YAG laser is also more complex resulting in operational errors and reducing the overall reliability of a staking process.

Lasers transmitting energy in the visible region of the spectrum (approximately 450–750 nm) are also being used for the staking process (U.S. Pat. No. 5,118,452). These lasers also require complex, expensive optics for their operation. Methods which use lasers transmitting energy in the visible range often require that the laser energy is coordinated with the color of the haptic to be attached. For example, if a blue haptic is to be attached, laser energy having a wavelength in the blue portion of the visible spectrum is used.

Some of the current methods used to stake the haptic to the optic require that an external piece of material is fused to the haptic. For example, the method disclosed in U.S. Pat. No. 5,118,452, requires that two intersecting bores be drilled on the periphery of the optic, wherein in one bore is inserted the haptic and in the other is inserted a separate anchor strand intersecting the haptic. A visible laser is then aimed at the intersection of the two bores fusing the strand to the haptic and, thus, staking the haptic to the optic.

Another method requiring the fusing of an external piece of material to the haptic is the method disclosed in U.S. Pat. No. 4,863,539. There the optic is swelled by being immersed in water and then an organic liquid, thereby, increasing the diameter of the peripheral and axial bores. After swelling, a haptic is inserted into a peripheral bore and a pin is inserted through the axial bore intersecting the inserted haptic. Afterwards, the organic liquid is removed and the optic contracts onto the haptic and pin. The pin is then heated and fused to the haptic.

Other methods of staking a haptic to an optic, such as the one disclosed in U.S. Pat. No. 4,104,339, require that the haptic comprise a wire. The wire haptic is inductively heated and simultaneously pressed into the optic, melting the optic material in the vicinity of the heated haptic and fusing the haptic to the optic. In another embodiment, bores are drilled on the periphery of the optic. The haptics are inserted into the bores. An inductively heated thin probe is then pushed through the base of the optic until it makes contact with the inserted haptic. The probes melts the optic and haptic material in its vicinity fusing the haptic to the optic.

To overcome the complexities associated with these methods, it is desirable to develop a system for staking a haptic to an optic that is highly reliable over an extended lifetime, that can use simple inexpensive optics, that is not required to be thermally efficient so as to allow for the controlled and uniform melting of the haptic to yield better uniformity and consistency, that does not require the use of laser energy having a wavelength in the visible region, that does not require a laser energy wavelength which is coordinated to the color of the haptic, that does not require the melting of an external piece of material for fusing the haptic to the optic, that does not require the swelling and subsequent reduction of the optic, and that does not require melting of the optic material.

SUMMARY OF THE INVENTION

A system for staking a haptic into an optic using a diode laser operating in the near infrared region is provided in the practice of this invention. To stake a haptic into an optic, a radial bore is drilled into the optic. An axial bore from the optic upper surface is drilled into the optic as well as to intersect the radial bore. An end portion of the haptic is inserted into the optic through the radial bore so that the inserted portion is exposed through the axial bore. An elliptical laser beam consisting of a diode laser beam having a wavelength near the infrared region and a coaxial diode aiming laser beam having a wavelength in the visible region is reconveyed to a collimator using a fiber optic power delivery system. The coaxial beams are collimated and are then focused using a microscope objective to a beam typically having a major diameter slightly larger than the diameter of the axial bore. The coaxial beams are then concentrically aimed through the axial bore onto the exposed haptic, melting the haptic material. The melted material flows up into the axial bore. The diode laser is then turned off, and the melted material is then cooled and coalesces forming an anchor staking the haptic into the optic. A charge coupled device (CCD) video camera connected to a monitor is positioned such that its optical axis is at a 45° angle with the optic. This camera provides a magnified view to aid the operator in the aiming and focusing of the laser beam onto the optic.

BRIEF DESCRIPTION OF THE DRAWINGS

FIG. 1A depicts a top view of an intraocular lens comprising an optic and two haptics.

FIG. 1B is a cross sectional view of the optic depicting the radial and axial bores.

DETAILED DESCRIPTION

Figure 2:
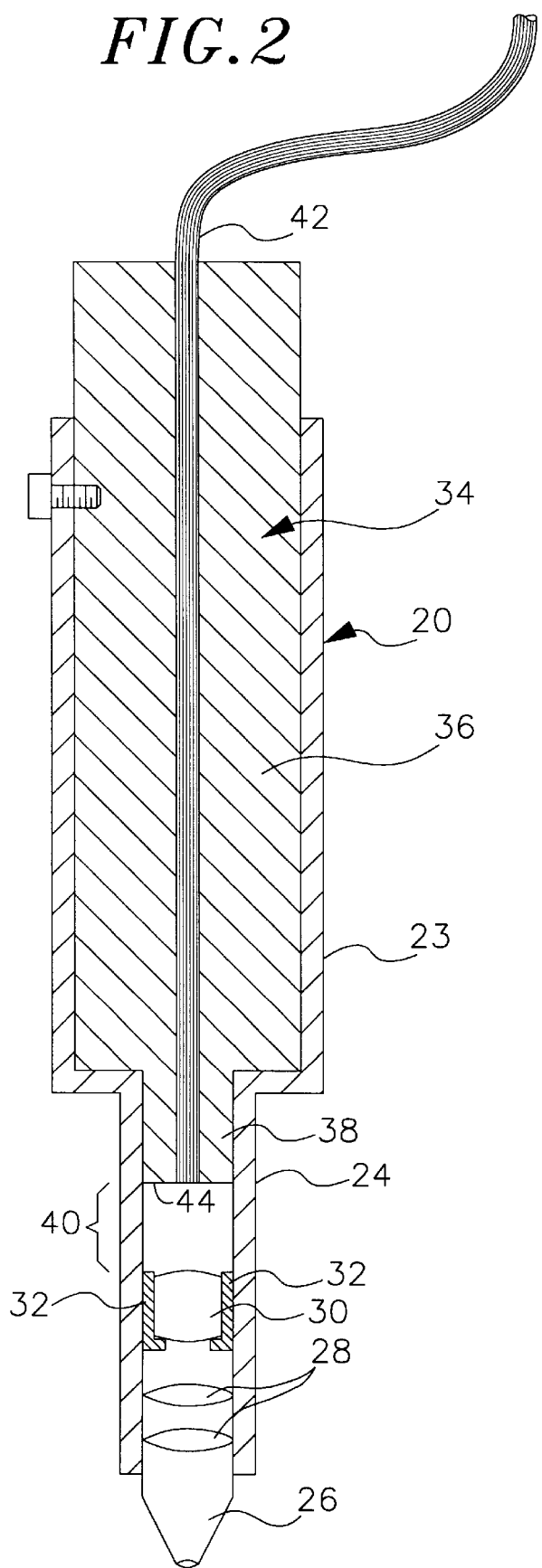
FIG. 2 is a cross sectional view of the launch optics microscope body assembly.

The present invention relates to a system for staking a haptic 10 to an optic 12 to form an intraocular lens 14. Intraocular lenses typically include a central lens section, referred to as the optic, for focusing the light onto the retina (FIGS. 1A and 1B). One or more supporting structures, called haptics, extend outwardly from the optic to align and stabilize the optic with respect to the pupil. Typically, the haptics comprise one or more filamentous or wire-like arms or loops which extend radially outwardly from the periphery of the optic.

The optic is circular and is typically made of a relatively filamentous material, such as polymethylmethacrylate (PMMA), or a soft, flexible semi-rigid material such as hydrogels, silicones and the like. Haptics, on the other hand, are usually, if not always, made from a rigid filamentous material such as polypropylene, known as Prolene®, PMMA or the like.

To insert a haptic into the optic prior for staking, a radial bore 16 is drilled from the outer periphery of the optic into the optic. An axial bore 18 is then drilled down from the optic upper surface perpendicularly until it intersects the radial bore. The axial bore typically has a diameter of 0.15 mm. The haptic end is inserted through the radial bore of the optic so that a portion of the haptic side wall is exposed through the axial bore. A diode laser is then concentrically aimed through the axial bore at the exposed haptic portion, heating and melting the haptic material. The melted portion of the haptic flows and penetrates both bores. The diode laser is then turned off, and the melted haptic material cools and coalesces into a solid bead or anchor, thus, fixing (staking) the haptic to the optic.

Diode lasers are used having an output wavelength near the infrared region. Preferably, a diode laser having a wavelength of about 800 nm or greater, but less than about 840 nm is used. There are many advantages associated with using a diode laser. Diode lasers are easy to set up. They are relatively inexpensive, they are reliable, have long lifetimes, and their beams can be delivered to the work site by simple fiber optic focusing optics, which are also relatively inexpensive.

A diode laser is inherently incoherent. However, because the diode laser is being used as a heat source rather than a optic source, this incoherence is not a disadvantage. Thus, specialized lenses are not required for keeping the light coherent. Additionally, diode lasers, which operate near the infrared region are not as thermally efficient as Nd:YAG lasers, which operate in the infrared region at 1060 nm. However, for the staking process, the lower thermal efficiency is advantageous because it permits slower and more uniform controlled heating leading to better consistency.

To deliver the diode laser beam to the staking point, a launch optics system of lenses has been developed. The launch optics have been fabricated using modified, off-the-shelf parts. By way of example, reference to components from particular manufacturers will be made. However, it is not the intention that the invention be limited to such components, as those of ordinary skill in the art will appreciate that the same function can be accomplished using components from different manufacturers.

Figure 3:
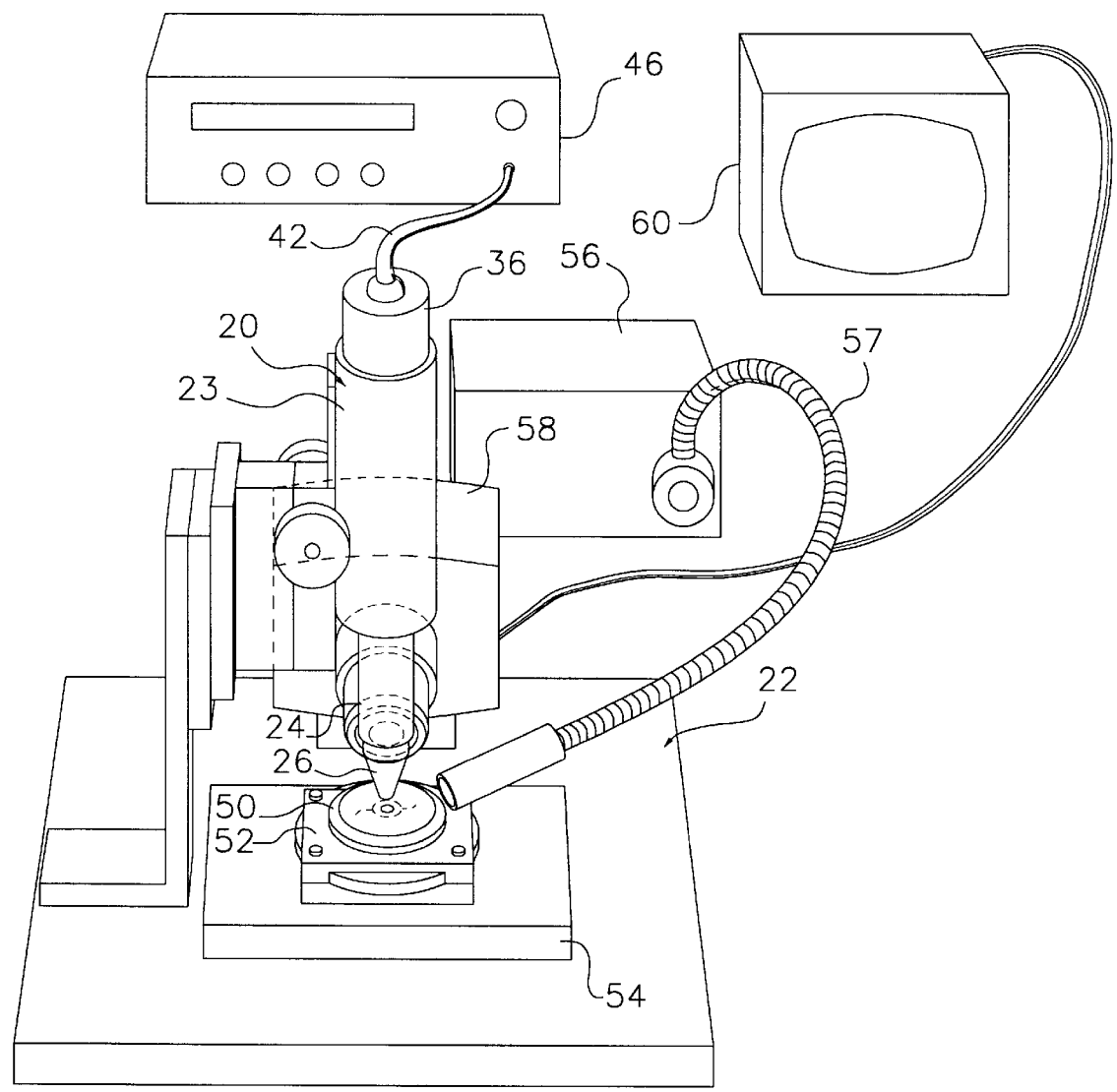
FIG. 3 depicts the diode laser staking apparatus or station.
Figure 4:
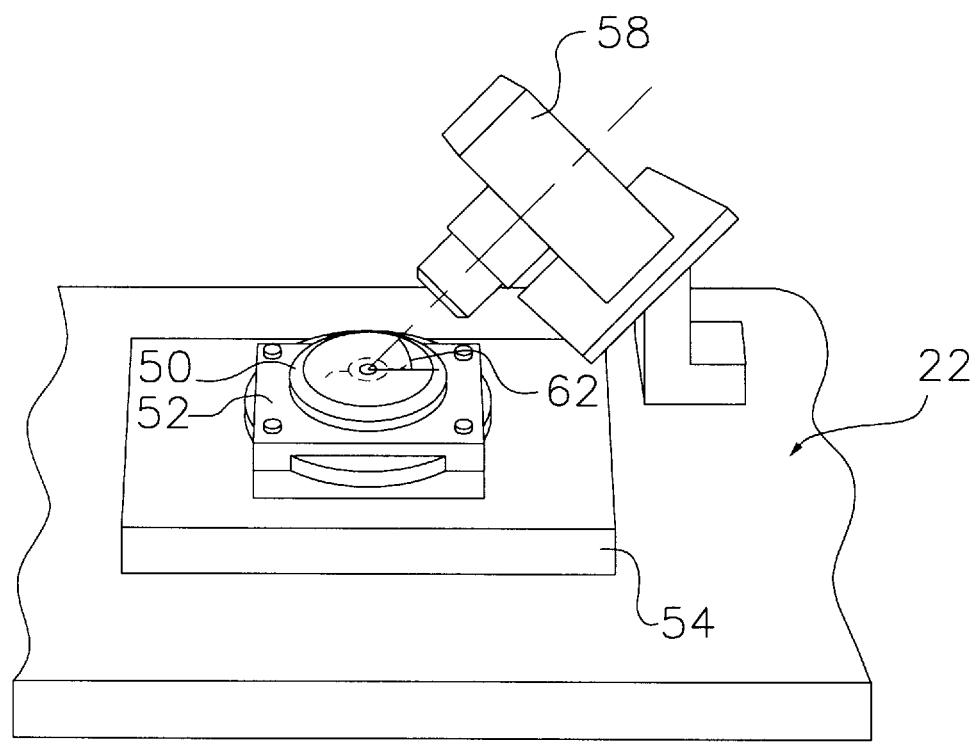
FIG. 4 depicts the CCD video camera with its optical axis at 45° to the optic horizontal plane.

To support and house the launch optics, a modified microscope body (Rolyn, 80.1120) 20 is used (FIG. 2). The body is adjustably connected to a launch optics fixture or support 22, allowing for micro adjustments to the position of the body relative to the fixture (FIG. 3). The body is modified in that its upper end portion is removed. The microscope body has an upper cylindrical section 23 co-centrally continuous with a lower cylindrical section 24 of smaller diameter. For descriptive purposes, the upper section is referred to herein as the wide section, while the lower section is referred to herein as the narrow section.

The head of the microscope is located at the lowest point of the narrow section of the microscope body. A 10X microscope objective (Rolyn, 80.3055) 26 is placed inside the narrower section abutting the head. A sleeve (not shown) may be placed inside the narrower section prior to the installation of the objective to provide support for the objective.

An objective (Melles-Griot, 06GLC003) 30 is placed within the narrow section proximate the microscope objective to function as a collimator. A brass sleeve 32 is placed prior to insertion of the collimator objective in the narrower section proximate the microscope objective, to provide support and allow for alignment of the collimator objective to the microscope objective. Once inserted, the collimator objective, or collimator objective and brass sleeve, may be cemented in place.

A ferrule 34 designed to slidably engage and fit within the microscope body is used to support a fiber optic cable laser delivery system. The ferrule is also comprised of two cylindrical sections, an upper cylindrical section 36 which is co-centrally aligned with a lower cylindrical section 38 of smaller diameter. The upper section outer diameter of the ferrule is slightly smaller than the wide section inner diameter of the microscope body. Likewise, the outer diameter of the lower section of the ferrule is also slightly smaller than the inner diameter of the narrow section of the microscope body. This allows the ferrule to slide within the microscope body. The length of the lower section of the ferrule is shorter than the length of the narrow section of the microscope body. The length of the lower section is designed so that when the ferrule is adjusted in place within the microscope body, the distance 40 between the upper surface of the collimator objective and the lowest end of the ferrule is equal to the back focal length of the collimator objective.

A fiber optic cable laser delivery system is used to transmit the laser beam from the laser source to the collimator objective. A preferred fiber optic launch cable 42 is an Opto-Power 0.4 mm fiber optic cable (Opto Power, OPC-F5-437). One end of this cable is fitted within the ferrule which radially supports the cable so that the cable is linearly aligned with the ferrule's longitudinal central axis. The end of the fiber optic cable supported by the ferrule is flush with the ferrule's lowest end 44. The other end of the fiber optic cable is connected to the laser source 46 (Opto Power OPC-A002-mmm-FCTS) (FIG. 3).

A diode laser source is required that can provide a visible diode laser beam. The beam must be visible to allow the aiming and positioning of the diode laser beam on the axial bore of the optic. Because diode lasers operating near the infrared spectrum are invisible, a laser source capable of simultaneously providing a laser beam with a visible or aiming beam is required. One such source is the Opto Power diode laser, Model OPC-A002-mmm-FCTS. This diode laser source provides a diode laser beam having an 820±20 nm wavelength simultaneously with a coaxial visible diode laser beam having a wavelength of about 670 nm.

A staking cap and collet (not shown) as part of a staking nest 52 are designed to retain two haptics within the optic. After insertion into the optic, the haptic total peak-to-peak distance is 13 mm and the haptics form an angle of 10° with the optic. In an alternative embodiment, a staking cap designed to retain a single haptic is used. The design of the staking cap is controlled by the types and sizes of haptics and optics being staked. The dimensions given herein are by way of example only. A loop holder 50 designed to mate over the staking cap is used to hold the haptics in place into the optic during handling and staking (FIG. 3). The staking nest is then placed underneath a microscope body on a platform 54 so that the laser beam emitted from the microscope body can be directed toward the axial bore of the optic. The platform is rotatably adjustable about its longitudinal and lateral axes for aligning the laser beam with the axial bore.

The laser beam must be directed onto the axial bore to heat and melt the exposed haptic. It is preferable that the laser beam have a diameter of about 0.2 mm so that the laser beam can fill the axial bore for efficiently melting the exposed haptic. Smaller diameter beams can be used, however, they will not deliver the energy over all of the exposed haptic area. Diode lasers have a beam with an elliptical cross section. Therefore, typically the laser is focused and adjusted such that its minor beam diameter is about 0.15 mm or greater, that is approximately equal to or greater than the diameter of the axial bore. Beams having a minor axis diameter of 0.6 mm have been successfully used. Beams with greater diameters can also be used. However, such beams may be inefficient due to the wasted energy, i.e., the energy not focused through the axial bore.

The diameter of the laser beam is a function of various factors including the diameter of the fiber optic cable delivery system, the collimator optics, and the microscope objective. The diameter of the laser beam that is incident on the back lens element of the 10X microscope objective, as reconveyed from the collimator objective, is effectively reduced. Proper beam size is assured by sharp focus of the elliptical beam.

An illumination system is used to illuminate the work area, i.e., the staking nest, including the optic and haptics. A gooseneck light guide (Dollan-Jenner BG2820) 57 in mounted on an illuminator (Dollan-Jenner 180/115) 56. The gooseneck light guide output end is directed at the work area. A CCD video camera (Marshall, V-7241C) 58 is also mounted on the launch optic fixture. The camera has a close-up lens (Marshall, V47816MZ) that can provide variable magnification up to 100X. These magnifying or zoom lenses can be motorized for foot switch operation.

For viewing, the video camera output is connected to a monitor (Toshiba, CM1300W) 60. In addition, the monitor can also be connected to a video tape recorder (not shown) to record the process. The camera is preferably color to provide for color viewing, which may be helpful because, in most situations, the optic is clear or slightly colored by a UV blocker while the haptic has a blue color. By positioning the camera optical axis at approximately a 45° angle 62 to the optic horizontal plane, the staking operator has a good view of the axial depth of the axial bore. The optic horizontal plane is the plane in line or parallel with the optic radial bores.

When the diode laser beam is applied to the axial bore, it melts the haptic and causes the melted haptic material to flow up the axial bore. The 45° angle view provides the operator with a perspective so that she/he can determine if the melted material has reached a level below the upper surface of the optic so that beam energy can be regulated accordingly to prevent overflowing. In other words, viewing of the staking process at a 45° angle gives the operator a reference by which to judge the location of the melted material within the axial bore.

To stake the haptic into the optic, first, the haptics are inserted into the optic and are retained in place by the staking cap. A loop holder is then mated over the staking cap to hold the optics and haptics in place during the nest handling and staking. The optic is positioned into the staking cap with its upper surface and its axial bores exposed. The staking nest, containing the optic and haptics, is then guided under the microscope body and locked in place. The aiming beam of the laser source is turned on to provide guidance for aiming the laser beam onto the axial bore of the optic. The operator is able to position the aiming beam onto the axial bore of the optic by looking at the beam's aim on the video monitor. A grid or cross hairs superimposed on the video monitor may be used to aid the operator in aiming the beam. The aim is controlled by adjusting the microscope or the platform supporting the staking nest. Preferably, the beam is aimed by micro adjustably positioning the staking nest under the aiming beam.

Once the aiming beam is aimed and focused directly onto the axial bore and onto the exposed side wall of the haptic, the diode laser is turned on. For this particular diode laser, the diode laser is adjusted to provide 1.15 Watts with a duration of 800 microseconds and a pulse interval of 200 microseconds. This is referred to as a multishot mode.

As discussed earlier, the travel of the melted haptic material through the axial bore can be viewed via the CCD camera video monitor. As the melted haptic material flows up through the axial bore toward the optic upper surface, the diode laser is turned off to prevent overflowing of the melted material onto the upper surface of the optic. The melted material is then allowed to cool and coalesce into a bead in both the axial bore and the radial bore, forming an anchor and staking the haptic onto the optic. The same procedure is then followed to stake the other haptic into the optic. With staking nests which allow for the retaining of both haptics, the nest is rotated 180° and the procedure is repeated.

Having now described the invention as required by the patent statutes, those skilled in the art will recognize modifications and substitutions to the elements of the embodiments disclosed herein. Such modifications and substitutions are within the scope of the present invention as defined in the following claims. For example, a two piece cylindrical microscope body can be used instead of a single piece body. The two piece microscope body comprises an upper piece concentric to a lower piece. The upper piece can adjustably slide relative to the lower piece. One of the pieces is adjustably mounted to the launch optics fixture. The ferrule is fitted within the upper piece and the microscope objective is placed within the lower piece. The collimator objective can be fitted on either piece. If fitted within the upper piece, the collimator is set a distance equal to its back focal length away from the laser power delivery system output end. If the collimator is fitted in the lower piece, the body pieces are adjusted relative to each other to separate the collimator objective from the power delivery system output end by a distance equal to the collimator back focal length.

What is claimed is:

1. A method for staking a haptic having a first end to an optic having an upper surface comprising the steps of:
    inserting the haptic first end into the optic;
    melting a portion of the inserted haptic first end using a diode laser beam having a wavelength in the range from about 800 to about 840 nm; and
    cooling the melted haptic to coalesce into a bead, anchoring the haptic to the optic.

2. A method for staking a haptic to an optic as recited in claim 1 further comprising the steps of:

forming a radial bore in the optic;

forming an axial bore through the optic upper surface intersecting the radial bore;

inserting the first end of the haptic into the radial bore and exposing said first end onto the axial bore; and melting a potion of the inserted first end of the haptic using the diode laser aimed at the haptic onto the axial bore.

3. A method for staking a haptic to an optic as recited in claim 2 wherein the step of melting further comprises use of an aiming visible laser beam, said aiming laser beam being coaxial with the diode laser beam having a wavelength from about 800 to about 840 nm, the method further comprising the step of controlling the aim of the coaxial beams by viewing the laser beams' aim with a CCD video camera.

4. A method for staking a haptic to an optic as recited in claim 3 further comprising the steps of:

connecting the CCD video camera to a video monitor; and viewing the coaxial laser beams' aim on the monitor.

5. A method for staking a haptic having a first end to an optic having an upper surface, comprising the steps of:

forming a radial bore in the optic;

forming an axial bore through the optic upper surface intersecting the radial bore;

inserting the first end of the haptic into the radial bore exposing a portion of the haptic through the axial bore;

collimating a diode laser beam having a wavelength in the range from about 800 to about 840 nm and a coaxial aiming beam using collimating means, said collimated beams having an elliptical cross-section;

focusing the collimated beams using a microscope objective to an elliptical beam having a minor diameter which is greater than the inner diameter of the axial bore;

directing the adjusted laser beam onto the axial bore to heat the exposed haptic portion and melt the haptic material; and allowing the melted haptic material to flow through both bores, said material coalescing into a bead and staking the haptic to the optic.

6. A method for staking a haptic to an optic as recited in claim 5 further comprising the step of delivering the coaxial beams from a laser source to the collimating means using a power delivery system.

7. A method for staking a haptic to an optic as recited in claim 6, wherein the step of delivering the coaxial beams to the collimating means comprises the step of connecting a fiber optic cable from the laser source to a location in line with the collimating means.

8. A method for staking a haptic to an optic as recited in claim 6 wherein the collimating means comprises a collimator, further comprising the step of fixing the distance between the collimator and the power delivery system to a distance equal to the back focal length of the collimator.

9. A method for staking a haptic to an optic as recited in claim 8 further comprising the step of aiming the coaxial laser beams onto the axial bore of the optic by viewing the location of the beams' aim using a CCD video camera focused at the optic.

10. A method as recited in claim 9 further comprising the step of aiming the optical axis of the CCD video camera at approximately a 45° angle to a horizontal plane of the optic parallel with the optic radial bores.

* * * * *